(12) United States Patent
Swinger

(10) Patent No.: US 8,500,283 B1
(45) Date of Patent: Aug. 6, 2013

(54) MICROSCOPE-ATTACHABLE ABERROMETER

(76) Inventor: Casimir A. Swinger, New York, NY (US)

( * ) Notice: Subject to any disclaimer, the term of this patent is extended or adjusted under 35 U.S.C. 154(b) by 133 days.

(21) Appl. No.: 12/798,394

(22) Filed: Apr. 2, 2010

Related U.S. Application Data

(60) Provisional application No. 61/211,743, filed on Apr. 2, 2009.

(51) Int. Cl.
*A61B 3/10* (2006.01)
*A61B 3/00* (2006.01)

(52) U.S. Cl.
CPC .................................... *A61B 3/1015* (2013.01)
USPC .............................. 351/212; 351/205; 351/245

(58) Field of Classification Search
CPC .............................. A61B 3/1015; A61B 3/0075
USPC .................. 351/206, 208, 221, 205, 212, 245
See application file for complete search history.

(56) References Cited

U.S. PATENT DOCUMENTS

| | | | |
|---|---|---|---|
| 4,597,648 A * | 7/1986 | Feldon et al. ................. | 351/212 |
| 5,486,892 A * | 1/1996 | Suzuki et al. ................. | 396/51 |
| 5,703,637 A * | 12/1997 | Miyazaki et al. ............... | 348/53 |
| 5,729,385 A * | 3/1998 | Nishida et al. ................. | 359/434 |
| 6,361,168 B1 * | 3/2002 | Fujieda .......................... | 351/208 |
| 6,382,795 B1 | 5/2002 | Lai | |
| 6,406,146 B1 | 6/2002 | Lai | |
| 6,460,997 B1 * | 10/2002 | Frey et al. ..................... | 351/211 |
| 6,575,572 B2 | 6/2003 | Lai et al. | |
| 7,448,752 B2 * | 11/2008 | Levine ........................... | 351/205 |
| 2005/0241653 A1 | 11/2005 | Van Heugten et al. | |
| 2005/0243276 A1 * | 11/2005 | Van Heugten et al. ....... | 351/205 |
| 2009/0103050 A1 * | 4/2009 | Michaels et al. .............. | 351/208 |

OTHER PUBLICATIONS http://www.photonics.com/edu/Term.aspx?TermID=3169.*
Juan Tabernero and Pablo Artal, Surface Reflections Reveal Hidden Eye Misalignment, Laser Focus World, Jun. 1, 2007.

* cited by examiner

*Primary Examiner* — Zachary Wilkes

(57) ABSTRACT

The present invention contemplates a new and improved wavefront aberrometer attachable to an ophthalmic microscope. The present invention also contemplates implementation of a long working distance and a large measurement range into the wavefront aberrometer. The present invention further contemplates to make it quick and easy to insert the wavefront aberrometer and to move it away from the working space of the ophthalmic microscope. The present invention still further contemplates implementation of a keratometry measurement to monitor the corneal status at the time of wavefront power measurement.

20 Claims, 3 Drawing Sheets

MICROSCOPE-ATTACHABLE ABERROMETER

This application claims the benefit of U.S. Provisional Application No. 61/211,743, filed on Apr. 2, 2009.

TECHNICAL FIELD

The present invention relates to an ophthalmic aberrometer attachable to an ophthalmic microscope. In particular, the present invention relates to a microscope-attachable aberrometer configured for intraoperative use in corneal (including refractive) and cataract surgery.

BACKGROUND

Ophthalmic aberrometers, known also as wavefront devices (of which there are multiple types based on several different physical principles, some initially developed primarily for ground-based astronomy) and surgical microscopes are both commonly employed in corneal and cataract surgery, typically as standalone instruments. They often are not even used in the same room as one another.

Corneal or limbal relaxing incisions (LRIs) have been used for years in corneal and cataract surgery, typically without the benefit of an intraocular measurement. Such incisions can, rather than correcting the desired amount of astigmatism, produce a new and unexpected vector resultant. Surgeons utilizing recent advancements in cataract surgical lenses, such as intraocular lenses (IOL's) for correction of astigmatism (toric IOL's) and for correction of both distance and near vision (presbyopia), such as accommodating IOLs and multifocal lenses (of complex surface structures), have found it helpful to make intraoperative wavefront measurements. Use of such lenses, often known as premium lens surgery, is at a price premium and demands increased intraoperative accuracy to avoid a later, secondary surgical procedure to correct for a lack of accuracy in the first procedure. Developments in femtosecond corneal and lens-based refractive surgery for example, may also benefit from the attachment of an ophthalmic aberrometer onto an ophthalmic microscope.

Aberrometry/wavefront technology is a highly sophisticated tool for characterization of the optical characteristics of the eye and it has the possibility of providing the enhanced accuracy demanded in more sophisticated corneal and cataract surgical procedures aimed at a specific optical outcome for an eye. The concept of correcting ophthalmic aberrations dates back to at least 1987.

A standalone ophthalmic aberrometer has its own positioning mechanism to align the instrument axis with the subject eye's visual axis, and thus it is typically too heavy and too big to attach onto a surgical microscope. Also, a standalone ophthalmic aberrometer typically has a short working distance in the range of 30-50 mm, while a surgical microscope typically has a working distance of 200 mm. A short working distance makes it easier for an ophthalmic aberrometer to have a larger measurement range of defocused power. On the other hand, a big working distance is necessary for a surgeon to perform eye surgery. This allows room for the surgeon to move instruments freely and to avoid touching an object other than the eye to avoid instrument contamination. Thus, to avoid any reduction of the clearance long used by the surgeon between the eye and the microscope, a clearance in which the surgeon's long experience was garnered, and to avoid placing a constraint on the surgeon's hand(s) which could increase tension or spasm and result in an inadvertent movement or less than desirable mobility, there is a need to redesign the ophthalmic aberrometer in order to be attachable onto a surgical microscope.

Surgical microscopes are designed with high quality optical components intent on optimizing the view for a surgeon performing delicate microsurgical procedures such as corneal, cataract and other intraocular surgery. It is thus preferable that the ophthalmic aberrometer shall not interfere in any way with either the working space or the image quality/optics of the microscope.

Though the aberrometer may be fixed to the microscope and possess utility for many anterior segment surgeons, some may not use such a device and others, such as vitreoretinal surgeons, may never need such a device attached to the microscope. In these cases, interference with both clearance and optical imagery could be a disadvantage. Economic issues could preclude duplicating surgical microscopes and thus make less than ideal the operating conditions for some surgeons or prevent the anterior segment surgeon from having access to an intraoperative aberrometer.

Aberrometric/wavefront measurement parameters, such as Zernike or Fourier coefficients, can arise from different elements in the optical system, the major ones being the cornea, the natural lens or an IOL of various types. Although it is typical that the surgeon has as the aim the correction or specific alteration of the wavefront of the total eye, information on the major aberration components such as defocus or astigmatism arising from the eye as a whole or a single component such as the cornea could have significant intraoperative utility. For example, a surgical procedure such as cataract surgery typically alters the intraocular pressure from the preoperative and postoperative condition. Any deformation of the cornea by altered intraocular pressure from the fluids and viscous materials will alter the ophthalmic wavefront measurement. This information is then used to make subsequent decisions regarding lens exchange or the placement of relaxing incisions to reduce astigmatism. Should the wavefront not be taken under the expected conditions of corneal power because of an unpredicted change in the corneal curvature, the LRIs might be executed erringly. If the corneal curvatures and power are known with the additional presence of a keratometer, these values can be taken into consideration along with the wavefront measurement in the decision making process to make appropriate adjustments.

SUMMARY

The present invention contemplates a new and improved wavefront aberrometer attachable to an ophthalmic microscope. The present invention also contemplates implementation of a long working distance and a large measurement/dynamic range into the wavefront aberrometer. The present invention further contemplates to quickly expedite insertion and removal of the wavefront aberrometer from the working space under and its extension behind the ophthalmic microscope. The present invention still further contemplates implementation of a keratometric measurement to monitor the corneal status at the time of wavefront power measurement, as this allows the surgeon to ascertain that the corneal curvature (s) are at or near their preoperative value(s) or taking their values into consideration prior to making corneal relaxing incisions to correct astigmatism or making adjustments to the intraocular lens based on the aberrometer reading.

Therefore, a first objective of the invention is a wavefront aberrometer that is attachable onto a surgical microscope for intraoperative measurement during corneal and cataract surgery. A second objective of the invention is a wavefront aber-

DETAILED DESCRIPTION

Figure 1:
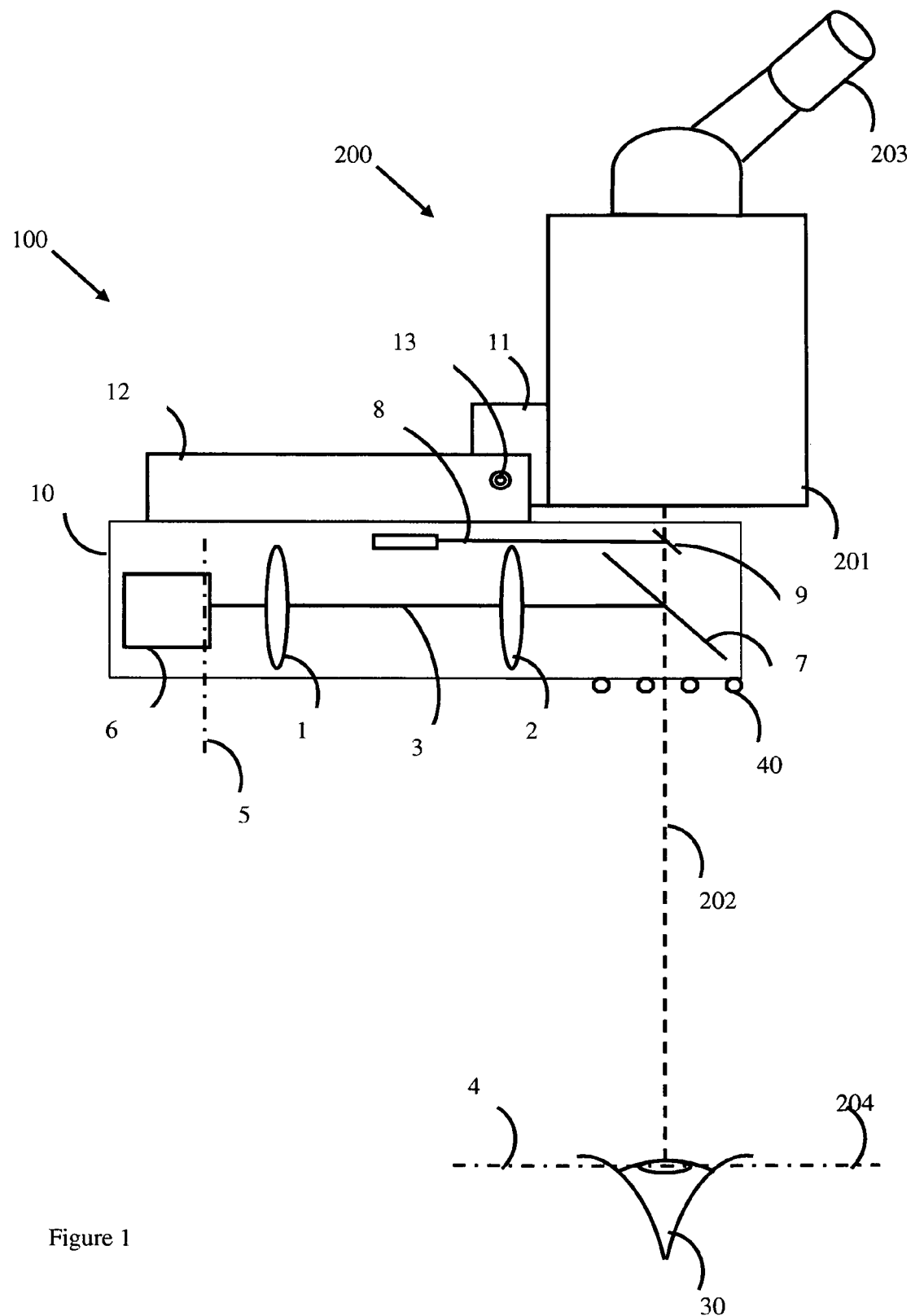
FIG. 1 shows an embodiment of a wavefront aberrometer attachable to an ophthalmic microscope.

FIG. 1 shows an embodiment of a wavefront aberrometer 100 attachable to an ophthalmic microscope 200. FIG. 1 is a side view of the ophthalmic microscope 200, which includes a microscope body 201, a left eyepiece 203, and a right eyepiece, which is not shown. The ophthalmic microscope 200 has a left viewing path and a right viewing path around the microscope's observation axis 202. The microscope 200 has an observation plane 204 predetermined with respect to the microscope body 201. The ophthalmic microscope 200 is movable via a positioning mechanism, which is not shown in the figure.

The microscope-attachable wavefront aberrometer 100 includes a first lens 1, a second lens 2, a wavefront sensor 6, a folding reflector 7, a probe beam 8, a turning mirror 9, an enclosure 10, a mounting block 11, an arm piece 12, and a mounting pin 13. The aberrometer 100 shall have physical dimensions comparable or smaller than the ophthalmic microscope 200. The aberrometer 100 shall also have weight substantially lighter than the ophthalmic microscope 200.

The first lens 1 and the second lens 2 form an afocal relay, which defines an optical axis 3, a front object plane 4, and a back image plane 5. The back image plane 5 is conjugated with the front object plane 4. The wavefront sensor 6 is placed at the back image plane 5 and is capable of receiving and measuring the wavefront aberration of a beam emerging from the object plane 4 and propagating through the afocal relay via the folding reflector 7. The design parameters for the optical afocal relay and wavefront sensor 6 are known to those skilled in the art.

The probe beam 8 is reflected via the turning mirror 9 to propagate along the observation axis 202. The probe beam 8 shall have a wavelength at the near infrared spectrum, ranging from 780 nm to 830 nm. The turning mirror 9 shall be small enough to place between the left viewing path and the right viewing path. The probe beam 8 shall have a small vergence and a small spot size at the object plane 4. The probe beam 8 is projected into subject eye 30 to generate an emerging beam from the eye 30 to be measured. The design specifications for the probe beam 8 are known to those skilled in the art.

Depending on the working distance and the measurement range of optical power, the folding reflector 7 may have an aperture smaller or bigger than the separation between the left and right observation paths of the microscope 200. When the aperture needs to be bigger than the separation between the left and right observation paths, the reflector 7 can be a thin dichroic mirror reflecting the probe beam 8 at near IR and transmitting visible light for microscope viewing.

The wavefront aberrometer 100 may further include a plurality of illuminators 40 disposed along a ring centered with the folded optical axis 202. The plurality of illuminators 40 can be made of an array of LEDs operated at infrared wavelength. The corneal reflection of the plurality of illuminators 40 can be employed for keratometry to measure the radius of curvature of the subject cornea. It is helpful to measure the corneal power prior an intraoperative aberrometer measurement. This way, the surgeon can avoid any cornea-induced wavefront error, such as corneal power change due to a change in intraocular pressure. The design concept and detection algorism of a keratometer are known to those skilled in the art.

Another application of the plurality of illuminators 40 is to observe or measure the alignment of intra-ocular elements via the so-called Purkinje images I, III and IV. The design concepts and the use of Purkinje images I, III and IV are known to those skilled in the art.

The plurality of illuminators 40 can be replaced with a Placido illuminator or other patterned spot illuminator. This way, corneal topography can be obtained via Placido image or patterned spot image. Corneal topographers can be useful for measurement of the corneal power and profile. The design concepts and the implementation of corneal topographers are known to those skilled in the art.

Figure 2:
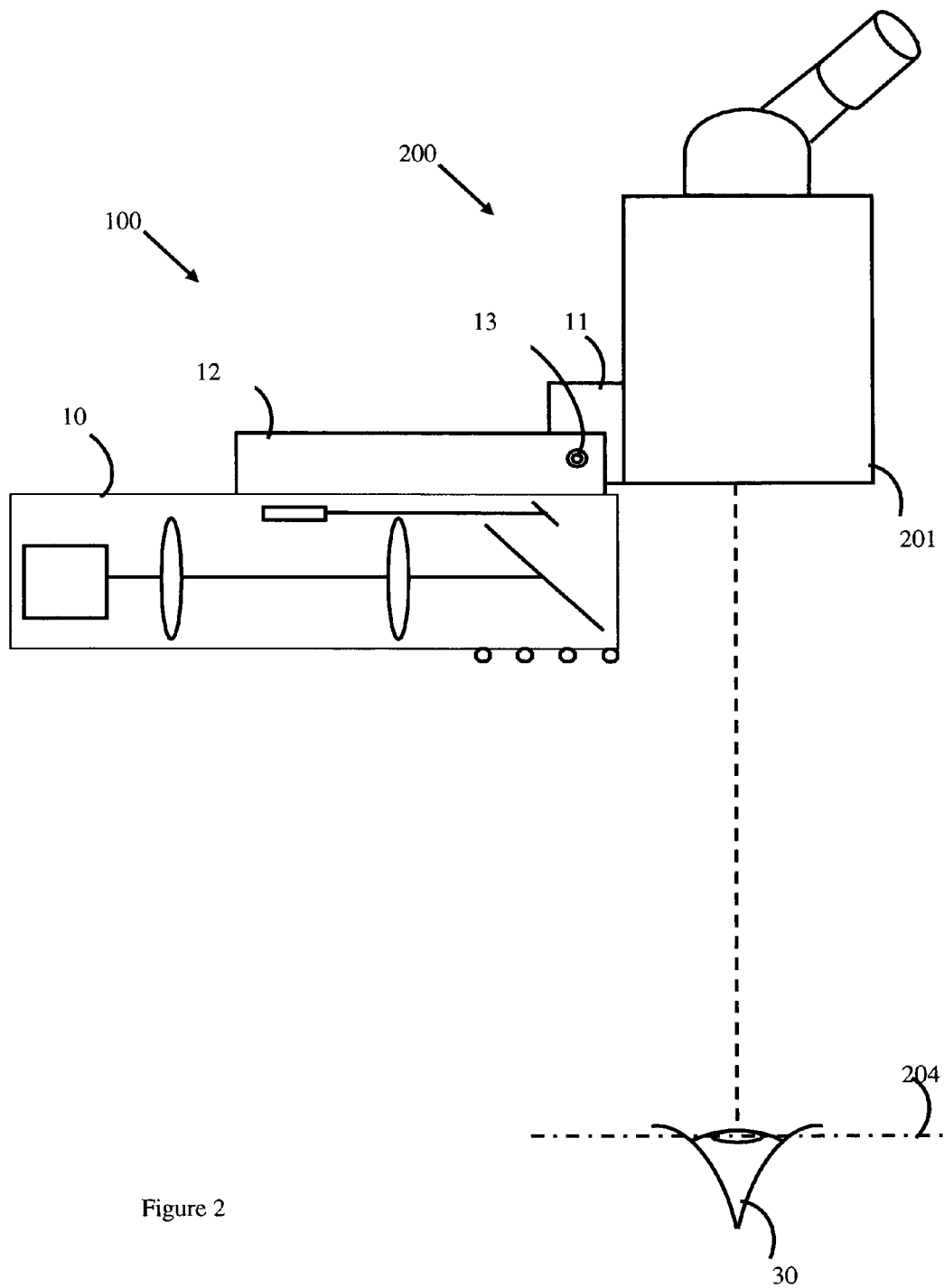
FIG. 2 shows an embodiment indicating that a wavefront aberrometer is slid away from its working position.

FIG. 2 shows an embodiment whereby the wavefront aberrometer 100 is slid away from its working position. In this embodiment, a sliding mechanism between the enclosure 10 and the arm piece 12 enables the wavefront aberrometer to slide away from its working position. This way, the microscope-attachable aberrometer takes no space from the surgical microscope 200 when eye surgery is taking place. The sliding mechanism can be adapted from a number of sliding mechanisms known in the art.

Figure 3:
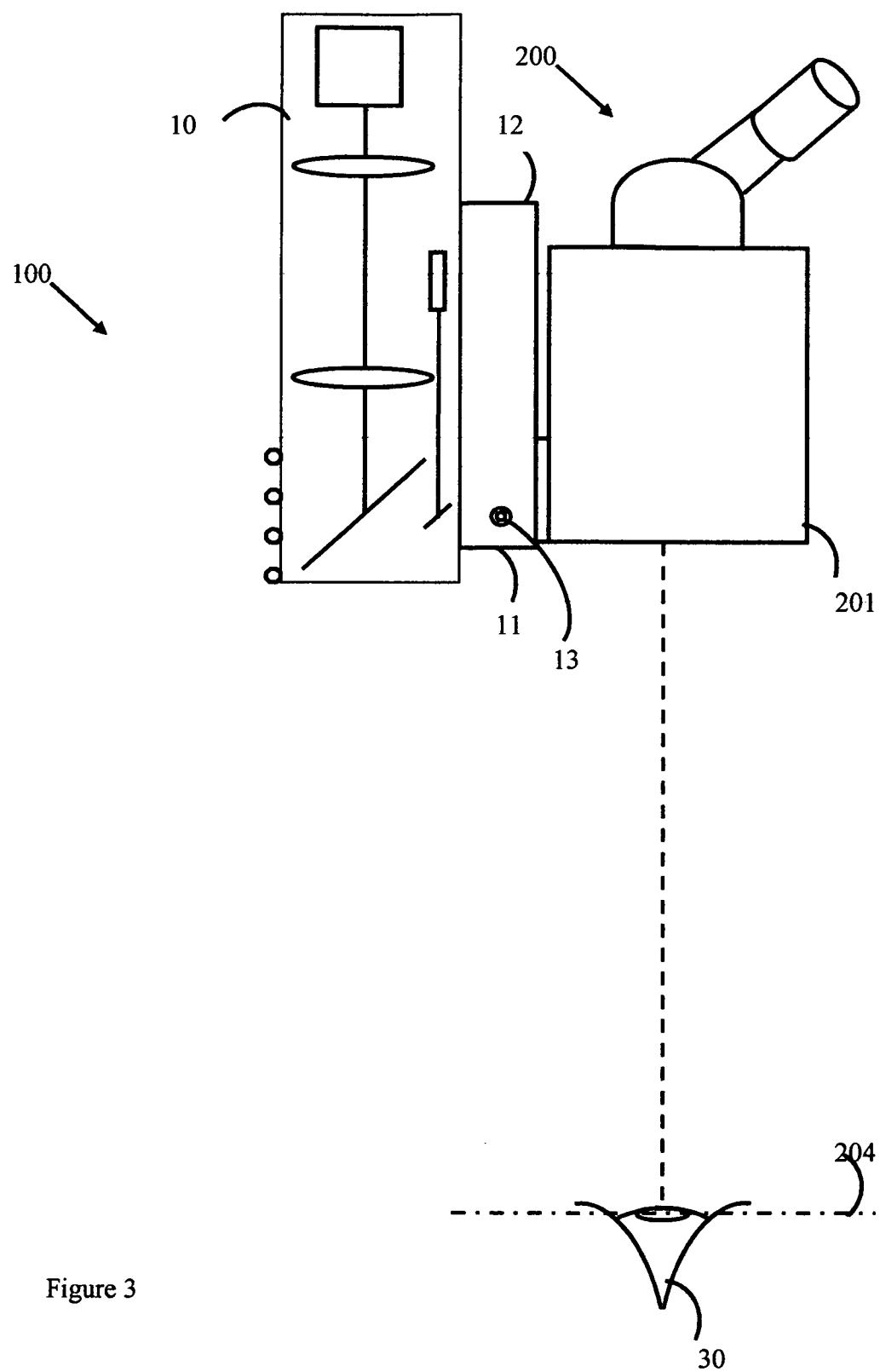
FIG. 3 shows an embodiment indicating that a wavefront aberrometer is slid away from its working position and further folded to clear working space for the ophthalmic microscope.

FIG. 3 shows an embodiment whereby the wavefront aberrometer 100 is slid away from its working position and further folded to clear working space for the surgical microscope 200. The sliding and folding mechanism can be adapted from a number of mechanisms known in the art.

It is understood that, the present disclosure includes only a few embodiments, other modifications and variations may be made without departing from the following claims.

PRIOR ART REFERENCES

Troutman R C, et al
Relaxing incision for control of postoperative astigmatism following keratoplasty. Ophthalmic Surg. 1980; 11:117-120

Swinger C A, et al
Prevention and Correction of Astigmatism: Intraocular lens implants. In: Cornea refractive surgery, and contact lens: Transactions of the New Orleans Academy of Ophthalmology. New York, N.Y.: Raven Press; 1987: 89-110.

U.S. Pat. No. 4,660,556 Apr. 28, 1987 C. Swinger, et al
Method and apparatus for modifying corneal buttons U.S. Pat. No. 6,325,792 Dec. 4, 2001 C. A. Swinger et al
Ophthalmic surgical laser and method U.S. Pat. No. 6,382,795 May 7, 2002 M. Lai
Method and apparatus for measuring refractive errors of an eye U.S. Pat. No. 6,406,146 Jun. 18, 2002 M. Lai
Wavefront refractor simultaneously recording two hartmann-shack images U.S. Pat. No. 6,575,572 Jun. 10, 2003 M. Lai, et al
Method and apparatus for measuring optical aberrations of an eye US2005/0241653 Nov. 3, 2005 Van Heugten et al
Integrated surgical microscope and wavefront sensor US2005/0243279 Nov. 3, 2005 Van Heugten et al
Integrated surgical microscope and wavefront sensor
US 20080269731 Oct. 30, 2008 C. A. Swinger, et al
Method and apparatus applying patient-verified prescription of high order aberrations

The invention claimed is:

1. An ophthalmic microscope-attachable aberrometer, comprising:
    an afocal relay defining an optical axis, a front object plane, and a back image plane, wherein said image plane is conjugated to said object plane;
    a Hartmann-Shack wavefront sensor positioned at said image plane and capable of measuring wavefront aberrations of a beam emerging from said object plane and propagating through said afocal relay;
    a folding reflector disposed between said afocal relay and said object plane;
    a probe beam projected along said optical axis and propagating toward said object plane;
    a mounting mechanism to attach said aberrometer onto said ophthalmic microscope such that said aberrometer, in its operation position, is movable with said ophthalmic microscope while said optical axis remains in alignment with an observation axis of said ophthalmic microscope; and
    a positioning mechanism enabling to position said optical axis to:
        a first position in alignment with said observation axis to perform wavefront measurement, and
        a second position away from alignment with said observation axis, to avoid interfering in any way with either working space or image quality of said ophthalmic microscope;
    wherein said positioning system enables back and forth positioning and repositioning said aberrometer at said first and second positions, and wherein said aberrometer remains attached and installed with said ophthalmic microscope.

2. An ophthalmic microscope-attachable aberrometer of claim 1, further comprising:
    a plurality of illuminators disposed along a ring centered with respect to said optical axis, wherein image of said plurality of illuminators is obtained to measure radius of curvature of a subject cornea, and wherein said plurality of illuminators are used for observing or measuring alignment of intraocular elements via Purkinje images I, III and IV;
    wherein said aberrometer is capable of measuring both wavefront aberrations and radius of curvature of a subject cornea, and wherein said Purkinje images can be used to determine whether said intraocular elements are properly aligned inside a patient's eye.

3. An ophthalmic microscope-attachable aberrometer of claim 1, wherein said object plane is located approximately 200 mm away from said afocal relay.

4. An ophthalmic microscope-attachable aberrometer of claim 1, wherein said probe beam is a non-coherent or a low-coherent light beam.

5. An ophthalmic microscope-attachable aberrometer of claim 1, wherein said Hartmann-Shack wavefront sensor is conjugated with said object plane.

6. An ophthalmic microscope-attachable aberrometer of claim 1, wherein said mounting mechanism is a machine part affixed onto the body of said ophthalmic microscope.

7. An ophthalmic microscope-attachable aberrometer of claim 1, wherein said positioning mechanism includes a sliding mechanism or a swinging mechanism, and wherein said sliding mechanism or swinging mechanism is to position said wavefront aberrometer with respect to said surgical microscope.

8. An ophthalmic microscope-attachable aberrometer of claim 1, wherein said ophthalmic microscope is a surgical microscope or a slit lamp microscope.

9. An ophthalmic microscope-attachable aberrometer, comprising:
    an afocal relay defining an optical axis, a front object plane, and a back image plane, wherein said image plane is conjugated to said object plane;
    a Hartmann-Shack wavefront sensor positioned at said image plane and capable of measuring wavefront aberrations of a beam emerging from said object plane and propagating through said afocal relay;
    a folding reflector disposed between said afocal relay and said object plane;
    a probe beam projected along said optical axis and propagating toward said object plane;
    a plurality of illuminators disposed along a ring or rings centered with respect to said optical axis, wherein image of said plurality of illuminators is obtained to measure radius of curvature of a subject cornea, and wherein said plurality of illuminators are used for observing or measuring alignment of intraocular elements via Purkinje images I, III and IV; and
    a mounting mechanism to attach said aberrometer onto said ophthalmic microscope such that said aberrometer, in its operation position, is movable with said ophthalmic microscope while said optical axis remains in alignment with an observation axis of said ophthalmic microscope;
    and
    a positioning mechanism enabling back and forth positioning and repositioning said aberrometer at a first position and a second position, wherein said aberrometer remains attached and installed with said ophthalmic microscope;
    wherein said aberrometer is capable of both measuring wavefront aberrations and measuring radius of curvature of a subject cornea, and wherein said Purkinje images can be used to determine whether said intraocular elements are properly aligned inside a patient's eye.

10. An ophthalmic microscope-attachable aberrometer of claim 9,
    wherein said first position is to position said optical axis in alignment with said observation axis to perform a wavefront measurement, and
    said second position is to position said optical axis away from alignment with said observation axis, to avoid interfering in any way with either working space or image quality of said ophthalmic microscope.

11. An ophthalmic microscope-attachable aberrometer of claim 9,
    wherein said first position is to position said object plane overlapped with the observation plane of said ophthalmic microscope to perform a wavefront measurement, and
    said second position is to position said object plane away from overlapped with the observation plane to avoid interfering in any way with either working space or image quality of said ophthalmic microscope.

12. An ophthalmic microscope-attachable aberrometer of claim 9, wherein said plurality of illuminators is incorporated to produce a keratometer image, in addition to said measuring said wavefront aberrations.

13. An ophthalmic microscope-attachable aberrometer of claim 9, wherein said plurality of illuminators is incorporated to produce, Purkinje images I, III and IV from various ocular surfaces.

14. An ophthalmic microscope-attachable aberrometer, comprising:
- an afocal relay defining an optical axis, a front object plane, and a back image plane, wherein said image plane is conjugated to said object plane;
- a Hartmann-Shack wavefront sensor positioned at said image plane and being capable of measuring the wavefront aberrations of a beam emerging from said object plane and propagating through said afocal relay;
- a folding reflector disposed between said afocal relay and said object plane;
- a probe beam projected along said optical axis and propagating toward said object plane;
- a topographer illuminator centered with said optical axis, wherein topography image is obtained to measure corneal power and profile, in addition to said measuring said wavefront aberrations; and
- a mounting mechanism to attach said aberrometer onto said ophthalmic microscope such that said aberrometer is movable with said ophthalmic microscope while said optical axis remains in alignment with an observation axis of said ophthalmic microscope; and
- a positioning mechanism enabling back and forth positioning and repositioning said aberrometer at a first position and a second position, wherein said aberrometer remains attached and installed with said ophthalmic microscope;
- wherein said aberrometer is capable of both measuring wavefront aberrations and measuring corneal power and profile, of which measuring corneal power and profile can be used to confirm the corneal status at the time of measuring wavefront aberrations.

15. An ophthalmic microscope-attachable aberrometer of claim 14,
- wherein said first position is to position said optical axis in alignment with said observation axis to perform a wavefront measurement, and
- said second position is to position said optical axis away from alignment with said observation to avoid interfering in any way with either working space or image quality of said ophthalmic microscope.

16. An ophthalmic microscope-attachable aberrometer of claim 14,
- wherein said first position is to position said object plane overlapped with the observation plane of said ophthalmic microscope to perform a wavefront measurement, and
- said second position is to position said object plane away from overlapped with the observation plane to avoid interfering in any way with either working space or image quality of said ophthalmic microscope.

17. An ophthalmic microscope-attachable aberrometer of claim 14, wherein said topographer illuminator is incorporated to produce an image of Placido rings.

18. An ophthalmic microscope-attachable aberrometer of claim 14, wherein said topographer illuminator is incorporated to produce an image of patterned spots.

19. An ophthalmic microscope-attachable aberrometer of claim 1, wherein said plurality of illuminators is made of an array of LED's.

20. An ophthalmic microscope-attachable aberrometer of claim 1, wherein said folding reflector is a dichroic mirror.

* * * * *